United States Patent [19]
Bale et al.

[11] Patent Number: 5,704,495
[45] Date of Patent: Jan. 6, 1998

[54] RELEASABLE RESTRAINING DEVICE

[76] Inventors: Michael S. Bale, Chelsea House 33623 Wildwood Dr., Abbotsford, British Columbia, Canada, V2S 1S2; James W. Lyons; Elinore G. Lyons, both of 34980 High Dr., Abbotsford, Britsh Columbia, Canada, V2S 4P6

[21] Appl. No.: 416,220

[22] Filed: Apr. 4, 1995

[51] Int. Cl.⁶ ............................................. A47G 29/00
[52] U.S. Cl. ............................................. 211/71; 248/311.3
[58] Field of Search ................................. 211/71, 75, 74, 211/88, 89; 248/311.3, 313, 314, 316.2, 312

[56] References Cited

U.S. PATENT DOCUMENTS

| | | |
|---|---|---|
| 3,653,624 | 4/1972 | Abel. |
| 3,938,769 | 2/1976 | Wetherbee. |
| 4,278,225 | 7/1981 | Phelps ........................ 248/311.3 |
| 4,326,648 | 4/1982 | Kieber ........................ 248/311.3 X |
| 4,909,467 | 3/1990 | San-Pao. |
| 5,016,845 | 5/1991 | Pellegrino. |
| 5,025,936 | 6/1991 | Lamoureaux ..................... 211/24 |
| 5,042,758 | 8/1991 | Roy. |
| 5,062,534 | 11/1991 | Neustat et al. ................. 211/89 X |
| 5,116,003 | 5/1992 | Gerhardt. |

FOREIGN PATENT DOCUMENTS

| | | |
|---|---|---|
| 1279610 | 1/1991 | Canada. |
| 1282376 | 4/1991 | Canada. |
| 1287816 | 8/1991 | Canada. |
| 1290725 | 10/1991 | Canada. |
| 2549554 | 5/1977 | Germany ..................... 211/77 |

*Primary Examiner*—Carl D. Friedman
*Assistant Examiner*—Creighton Smith
*Attorney, Agent, or Firm*—Oyen Wiggs Greeen & Mutala

[57] ABSTRACT

This invention relates to a novel restraining device for releasably restraining containers. A restraining device for an object having a base and a top, said restraining device having a base, back and top comprising: (a) a first restraining member associated with the back for releasably securing and applying a force to the base of the object; and (b) a second restraining member associated with the back for releasably restraining the top of the object and applying a restraining force on the top of the object, to thereby releasably secure the object in the restraining device.

18 Claims, 13 Drawing Sheets

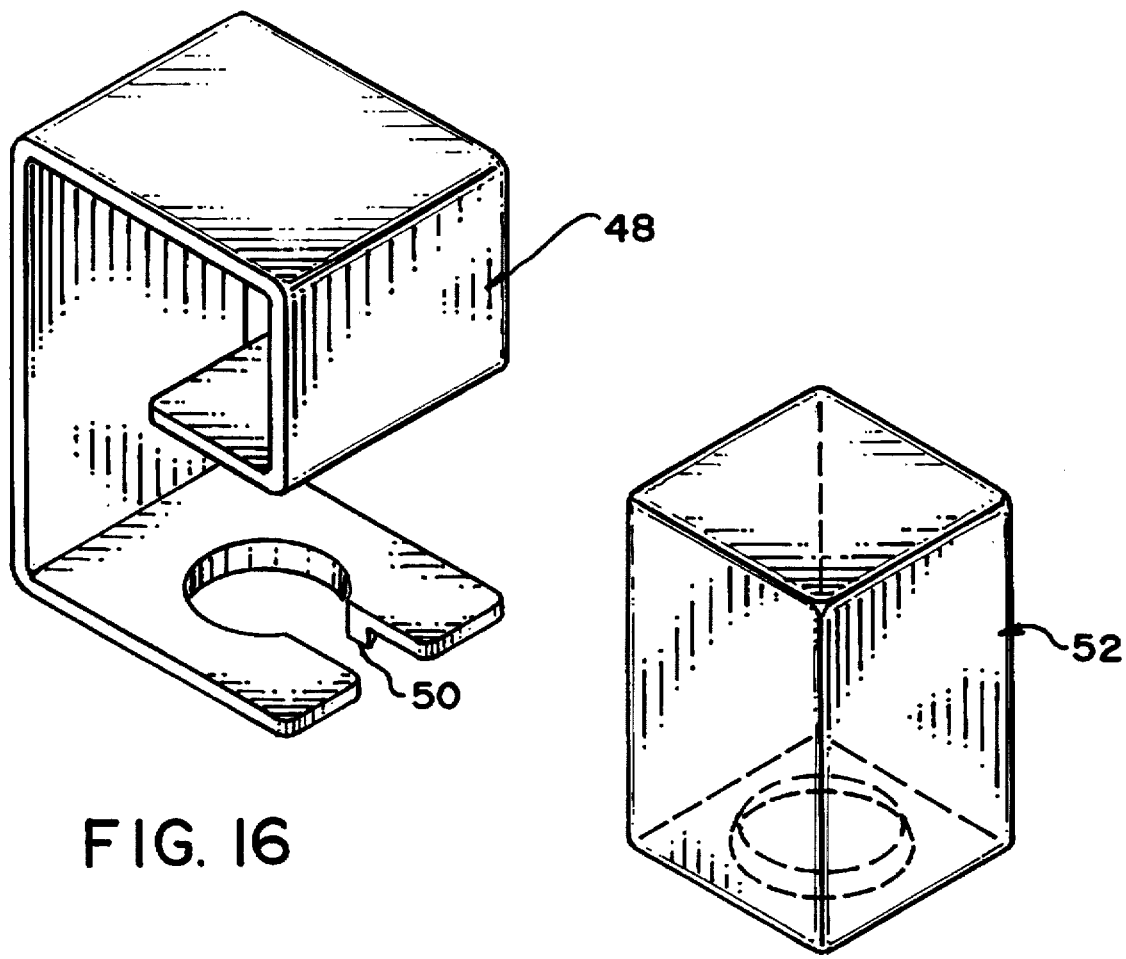
FIG. 16
FIG. 17
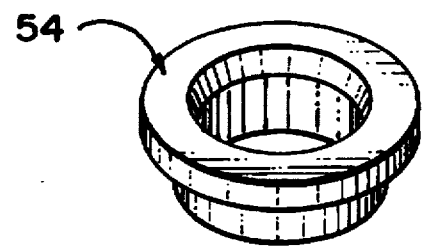
FIG. 18

RELEASABLE RESTRAINING DEVICE

FIELD OF THE INVENTION

This invention relates to a novel releasable restraining device for securing and holding objects and containers in a structure which permits ready access to and release of one or more of the containers and easy access to the objects or containers. The device may be mounted on a wall or portable frame so that in the case of containers, ready access can be made to the contents of each container within the restraining device.

BACKGROUND OF THE INVENTION

Economic factors within the health care industry have dictated that medical procedures be carried out with as few attending medical personnel as possible. Thus, it is now customary for surgeons to carry out many minor procedures without the assistance of an attendant nurse. Whenever a surgical procedure is performed it is imperative that sterile conditions prevail to prevent infection. During the course of a particular procedure, a physician may need to access one or more medications from various sterile containers. These containers are usually stored in a convenient drawer of a nearby cabinet. It is extremely awkward and inconvenient for the surgeon, during the course of a suturing procedure to find that he has to access medications in the drawer or a cabinet and, at the same time, maintain sterility in the operative area. It would thus be extremely helpful to the surgeon if a device existed which would enable the containers to be mounted in a convenient manner so that easy access could be achieved without the necessity of opening drawers and cupboards.

Such a device would have application in many areas of the health care system including hospitals, emergency rooms, ambulances and physician's clinics. There are many other situations in which such a device would have direct application, such as in chemical laboratories and automotive services where it would be desirable to have easy access to fluid filled containers mounted within a secure frame. In addition, it would be desirable that the containers could be easily released from the frame so that the material could be replenished once used.

The following patents are relevant or of interest to the field of technology of the invention.

| Country | Patent Number | Inventor | Issue Date |
|---------|--------------|----------|------------|
| U.S.A. | 3,653,624 | Abel | 4 April 1972 |
| U.S.A. | 3,938,769 | Wetherbee | 17 February 1976 |
| U.S.A. | 4,909,467 | Shan-Pao | 20 March 1990 |
| Canada | 1,279,610 | Avery | 29 January 1991 |
| Canada | 1,282,376 | Mawhirt | 2 April 1991 |
| U.S.A. | 5,016,845 | Pellegrino | 21 May 1991 |
| Canada | 1,287,816 | Rowse | 20 August 1991 |
| U.S.A. | 5,042,758 | Roy | 27 August 1991 |
| Canada | 1,290,725 | Guala | 15 October 1991 |
| U.S.A. | 5,116,003 | Gerhardt | 26 May 1992 |

Abel discloses a support device for gripping a bottle neck in an upright position. The opening for the bottle neck is circular and open at the front. The rear of the bottle holding device can be mounted to fit different mounts and maintain the neck of a bottle in an upright position.

Abel does not disclose multiple openings for storing a plurality of bottles. Also, there is no capability for storing the bottles in an inverted position, or applying a restraining force on the bottle base when in an inverted position.

Wetherbee describes an inverted bottle holding device with an overall C-shape. Wetherbee demonstrates the use of a top planar face to hold the bottle in place. FIG. 2 of Wetherbee shows a space between the upper plate and the bottle base so that no pressure is applied to the bottle base. Further, the rack is closed from the front. The base of the rack has circular closed holes (see FIG. 3) rather than holes which are open on one side.

Shan-Pao describes a scissor-action bottle and tool holding device which is mounted on a vertical surface by a plate. The bottle holding portion can be pivoted relative to the plate. Shan-Pao does not disclose a C-shaped device for holding a plurality of bottles in either an upright or inverted position. Further, Shan-Pao discloses a specific type of bottle neck holding mechanism. Finally, Shan-Pao does not disclose any mechanism for restraining the base of the bottle.

SUMMARY OF THE INVENTION

The invention is directed to a restraining device for an object having a base and a top, said restraining device having a base, back and top comprising: (a) a first restraining member associated with the back of the device for releasably securing and applying a force to the base of the object; and (b) a second restraining member associated with the back of the device for releasably restraining the top of the object and applying a restraining force on the top of the object, to thereby releasably secure the object in the restraining device.

The restraining device can have a C-shaped configuration, the lower limb of the C comprising the first restraining member which can releasably secure and apply a force to the base of the object, the upper limb of the C comprising the second restraining member which can releasably secure and apply a restraining force against the top of the object, and the stem of the C being the back of the restraining device.

The object to be releasably restrained can be a container which can have a neck and a base. The upper limb of the restraining device can have formed therein at least one opening which corresponds in shape and accommodates the neck of the container, whilst the lower limb can be resilient and can apply a restraining force to the base of the container.

The C-shaped restraining device can be constructed of two separate elements, which can be adjusted in position relative to one another to provide varying distances between the upper limb and the lower limb. The two separate elements can be adjusted in position relative to one another by means of a slot formed in one of the elements, and a restraining securing mechanism extending through the slot and securing the first restraining element to the second restraining element. The opening can have a removable collar which can fit around the neck of the container.

The C-shaped restraining device can be constructed in three separate elements, two of which elements make up the upper limb of the restraining device and which can be individually adjusted in position relative to one another and to the lower limb to provide varying distances between the upper limb and the lower limb of the restraining device.

The restraining device can include a protective shield extending from a free edge of the upper limb of the restraining device and extending downwardly to protect at least a portion of the open side of the C-shaped restraining device.

The upper limb of the C-shaped restraining device can be secured to a back of the C-shaped restraining device by a hinged mechanism and tension to the container achieved by a spring mechanism. Spring means for exerting a downwardly force on the upper limb can be connected between the upper limb and another part of the C-shaped restraining device. The spring can be of various types and include a coil spring, a spring steel clip, or a pair of adjustable screws.

The upper limb can have formed therein at least two openings spaced from one another, and a slot can be present between each opening.

The restraining device can include a perforated gasket which can fit in the opening, and releasably secure the neck of the container to the restraining device.

The restraining device can include a spacer which can fit between the base of the container and the lower limb, and thereby accommodate one or more containers which are shorter in length than the dimensions between the upper and lower limbs, and a releasable collar fitted around the circumference of the opening for releasably securing the neck of the container.

The restraining device can include a second restraining device of smaller size for receiving a container of smaller size and for fitting into the space between the upper and lower limbs of the C-shaped restraining device.

The restraining device can include a plurality of restraining devices of smaller size fitted in series into the space between the upper and lower limbs of the C-shaped restraining device. The restraining device can include a plurality of spacers and a plurality of collars.

The restraining device can have a plurality of openings and a plurality of perforated gaskets for fitting into the plurality of openings of the upper limb of the restraining device. The plurality of perforated gaskets can each include an opening therethrough for fitting about the respective necks of a plurality of containers. The opening in the plurality of gaskets is custom designed to accommodate the respective necks of a plurality of containers. The openings can be circular, square shaped or star shaped.

BRIEF DESCRIPTION OF THE DRAWINGS

In drawings which illustrate specific embodiments of the invention, but which should not be construed as restricting the spirit or scope of the invention in any way:

FIG. 16 illustrates an isometric view of a small size restraining device with a collar below the opening in the lower shelf of the small restraining device.

FIG. 17 illustrates an isometric view of a box shaped spacer for releasably connecting the base of a small container to the upper shelf of the restraining device.

FIG. 18 illustrates an isometric view of a container neck collar, which fits the neck of a container and is used in association with the spacer illustrated in FIG. 17.

DETAILED DESCRIPTION OF SPECIFIC EMBODIMENTS OF THE INVENTION

The primary objective of the restraining device is to provide a support frame (restraining structure) for the stabilization and releasable fixation of specific containers, usually containing liquids, or for securing other objects, such as spherical or cubical objects, in such a manner as to provide convenient and easy access to the contents of the containers, or to the objects themselves. Immobilization and releasable fixation of a container in the restraining device is achieved by securing the neck of the container in a purpose designed aperture in the top or bottom of the restraining device, as the case may be, and applying by means of the opposite bottom or top of the restraining device, as the case may be, a force to the base of the container exerted by pressure from the bottom or top of the frame. The restraining device can be mounted upright or in an inverted position.

The restraining device can be a C-shaped structure (frame) consisting of a top, bottom and back. In one aspect, the device can be made from a synthetic polymer which, when molded in the configuration described, possesses inherent elasticity which enables an object, such as a container, to be secured when appropriately placed between the top and bottom of the frame. The top of the frame, or the bottom if the frame is inverted, contains one or more apertures which are custom designed to accommodate the neck or necks of the appropriate container(s). Insertion of the neck of each container into the custom designed aperture results in immobilization (securement) of the neck of the container. The base of the container is releasably fixated as a result of a force being applied to the base of the container due to the inherent elasticity of the plastic C-shaped frame. The bottom of the frame (or the top of the frame if inverted) may be smooth, recessed or open to accommodate various configurations of the base of the container. As a result of the immobilization of the neck of the container into the top of the device (or the bottom if the frame and container are inverted) and the application of a restraining force to the base of the container from the bottom or top of the restraining device, the container is fully restrained and secured. The front of the restraining device may be used for mounting, carrying or viewing the containers. Access to the containers may be achieved from the top, bottom or sides of the restraining device. The entire restraining device, and the containers may be mounted in a horizontal, vertical, upright or inverted manner, as required.

Figure 1:
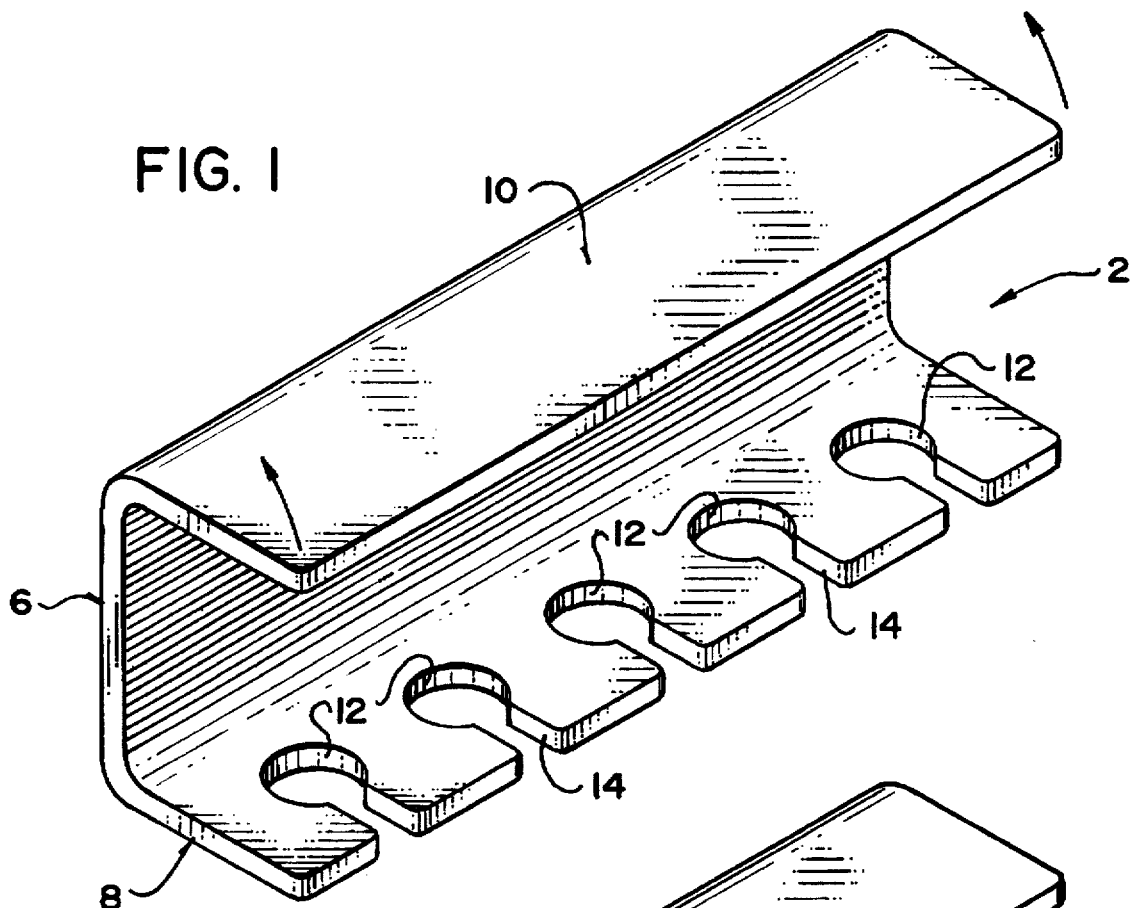
FIG. 1 illustrates an isometric view of a restraining device.

FIG. 1 illustrates an isometric view of the restraining device in an inverted position. The restraining device 2 is constructed with a back plate 6 which supports a lower shelf 8 and an upper shelf 10. The lower shelf 8 has therein a row of spaced circular recess openings 12, with slots 14 between the openings 12 and the fronts of each lower shelf 8. The upper shelf 10 is constructed of a resilient material such as acrylic polymer which exerts a downward force if moved upwards, or an upward force if deformed downwards. The intersections between the upper shelf 10, back plate 6 and lower shelf 8 are curved to ensure multiple flexes without stress cracks, which would occur more quickly if the intersections were square, thereby focusing the stress at the corners.

Figure 2:
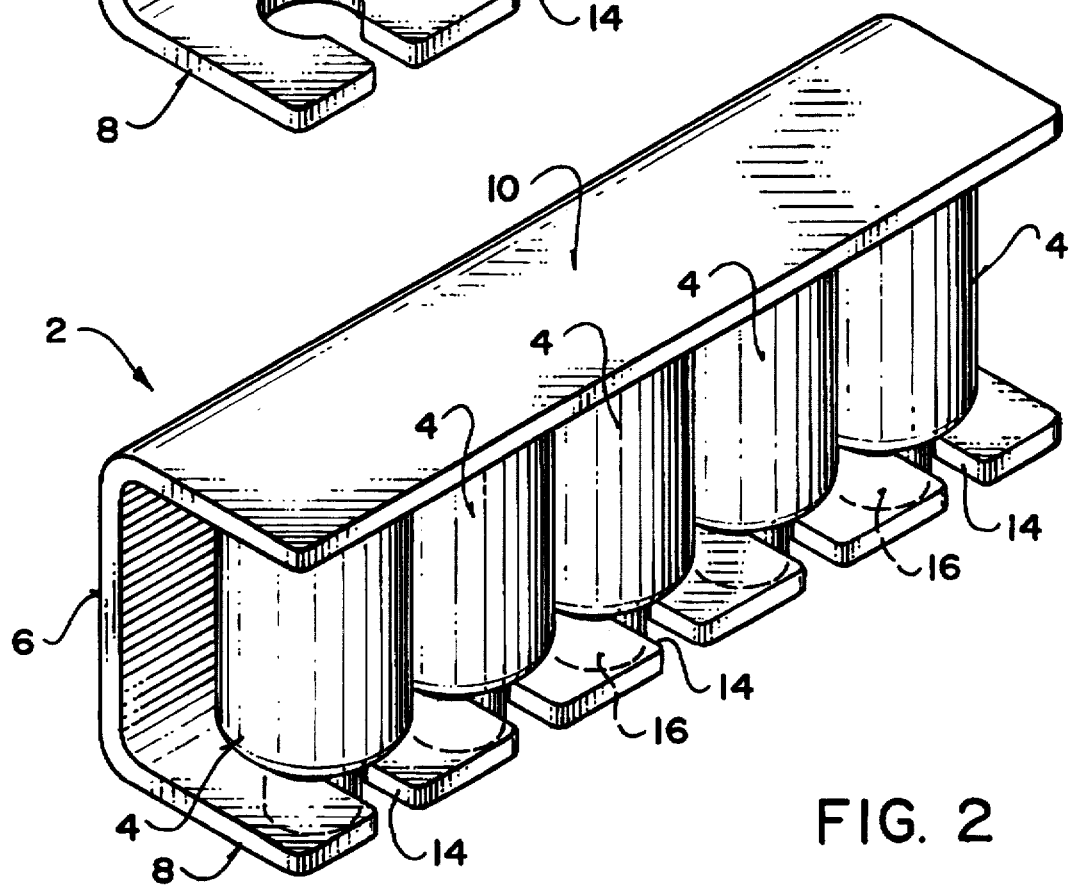
FIG. 2 illustrates an isometric view of a restraining device holding five containers in inverted position.

FIG. 2 illustrates an isometric view of the restraining device with five containers in place in inverted position. As seen in FIG. 2, the restraining device 2 is holding a row of five containers 4. The containers 4 are inverted with the necks thereof securely held in the lower shelf 8, and the corresponding openings 12, while the bases of the containers are held under a downward force by the upper shelf 10. The shapes of the openings are customized to snugly secure the necks of the containers.

Figure 3:
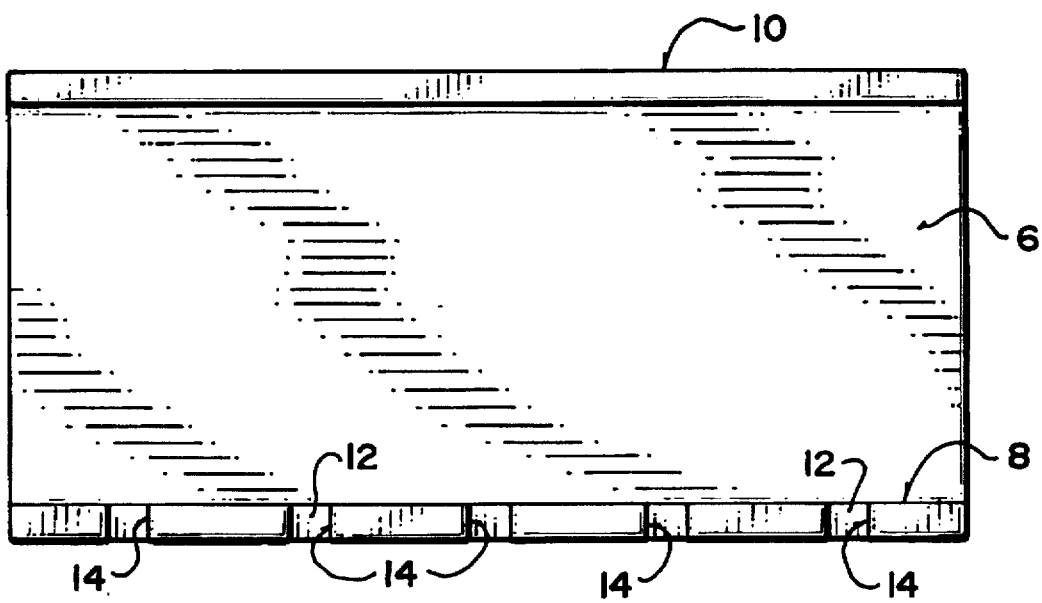
FIG. 3 illustrates a front view of the restraining device.

FIG. 3 illustrates a front view of the restraining device 2. The upper shelf 10 is mounted at the top of the back plate 6 while the lower shelf 8 is mounted at the bottom of the back plate 6.

Figure 4:
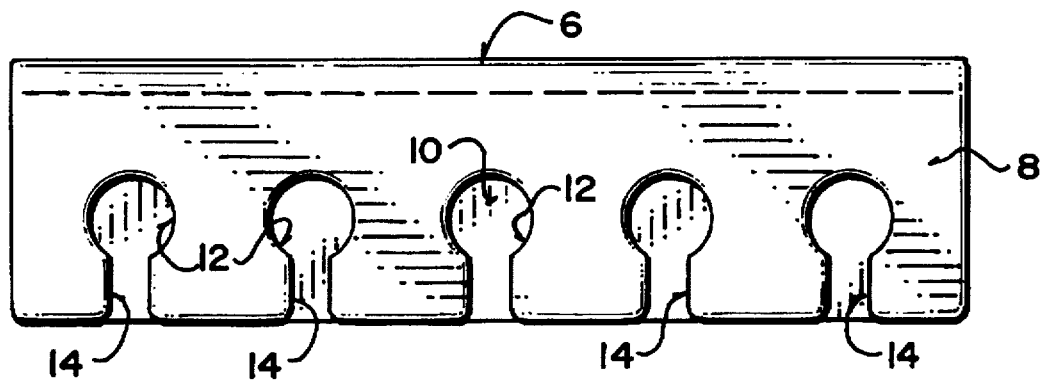
FIG. 4 illustrates a bottom view of the restraining device.

FIG. 4 illustrates a bottom view of the restraining device 2. The lower shelf 8 has formed therein a row of spaced circular openings 12, with respective slots 14 extending from the respective openings 12 to the front edges of the lower shelf 8.

It will be understood that the openings 12 need not necessarily be circular in configuration. They can be formed in the shape of hexagons, triangles, rectangles, or with ribs around the circumference thereof, for holding and securing the neck of the appropriate container. It will also be understood that the slots 14 need not necessarily be present. In other words, the lower shelf 8 can be solid along its front edge, and the openings 12 completely enclosed, or partially open at the front ends. The number of openings in the restraining device and the length of the restraining device can be varied as required. The openings 12 may be of different diameters and of different conformations in accordance with the design of the appropriate container.

Figure 5:
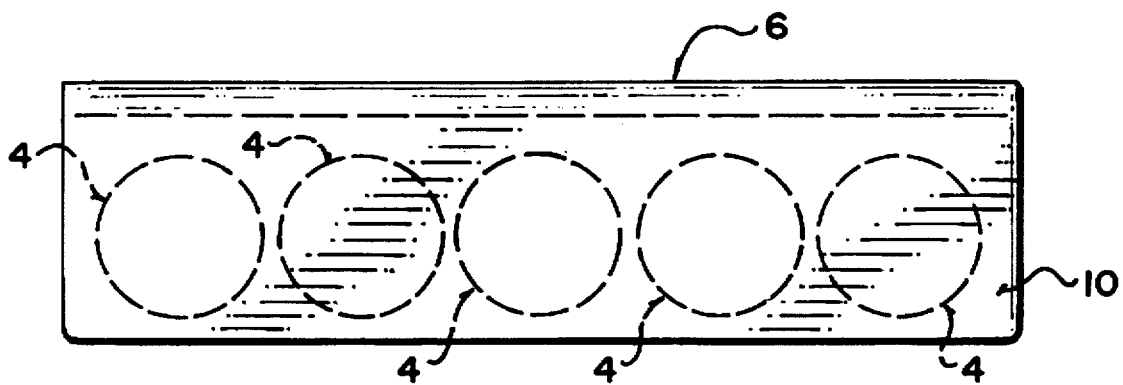
FIG. 5 illustrates a top view of the restraining device.

FIG. 5 illustrates a top view of the restraining device with the top shelf 10. The circumferences of the five containers 4 are shown in circular dotted lines.

Figure 8:
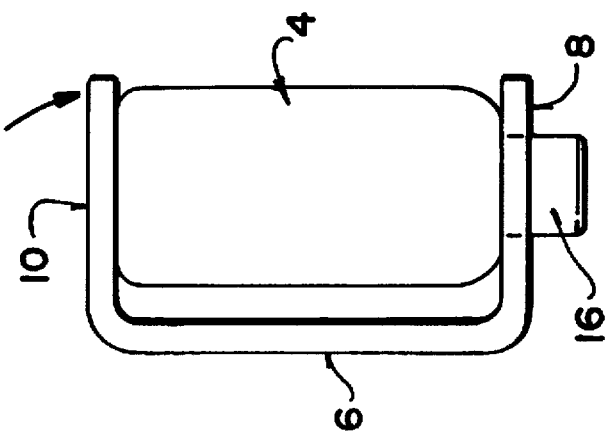
FIGS. 6, 7 and 8 illustrate in sequence the manner in which an inverted container is loaded into the restraining device.
Figure 7:
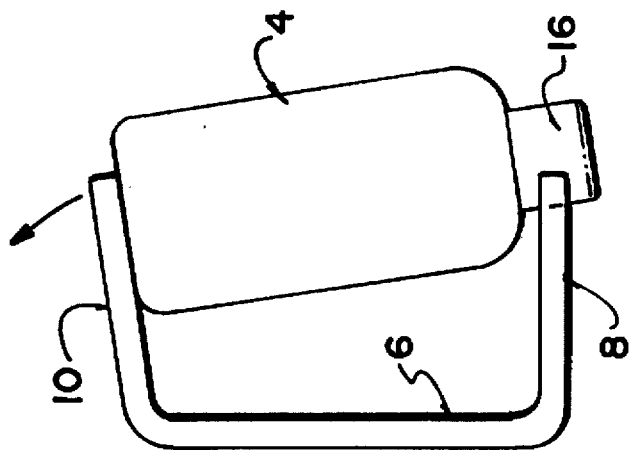
Figure 6:
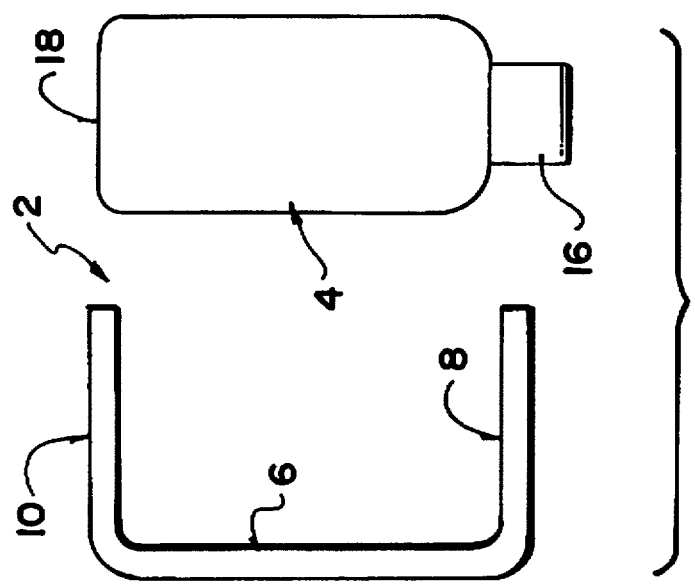

FIGS. 6, 7 and 8 illustrate in sequence the manner in which an inverted container is loaded into the restraining device. FIG. 6 illustrates a side view of a restraining device with back plate 6, bottom shelf 8 and top shelf 10. The inverted container 4 with the neck 16 extending downwards and the base 18 extending upwards, is shown at the right of the restraining device 2. It will be understood that the restraining device can be inverted compared to the orientation shown in FIG. 6, in which case the container is loaded into the device in an upright position. The restraining device can also be mounted to a ceiling, bottom of a shelf, or top of a shelf or tabletop, so that it is horizontal, with containers on the top, or upside down with the containers facing down, as the case may be.

FIG. 7 illustrates a side view of the container 4 being placed in the restraining device 2. The configuration illustrated in FIG. 7 is subsequent in time to the configuration illustrated in FIG. 6. As seen in FIG. 7, first the upper shelf 10 is forced upwardly by the base 18 of the container 4, as indicated by the arrow. Then, the inverted neck 16 of the container 4 is moved inwardly so that the neck 16 fits partially into the slot FIG. 8 illustrates a side view of the container 4 fully installed in the restraining device 2. The configuration illustrated in FIG. 8 is subsequent in time to the configuration illustrated in FIG. 7. As seen in FIG. 8, the base of the container 4 has been fully moved underneath the upper shelf 10, the inverted neck of the container 4 has been fully moved to a position so that it extends downwardly through the opening 12, in which position the upper shelf 10, due to natural resistance, is then able to move to its normal lower horizontal position. The upper shelf 10, at least, is normally designed of resilient material so that it exerts a downward force on the base 18 of the container 4, thereby holding the container 4 and the neck 16 in secure position in the restraining device 2. The container 4, in an inverted position, enables fluids to be readily withdrawn from the interior of the container 4 through the inverted neck 16. If desired, a connecting tube, or a cap and tube with a valve, can be secured to the inverted neck 16 of the container 4. It will be recognized that the design of container 16 illustrated in FIGS. 6, 7 and 8 is only one of many potential container designs, and accordingly, the restraining device 2 can be modified as required to accommodate different container shapes.

Figure 9:
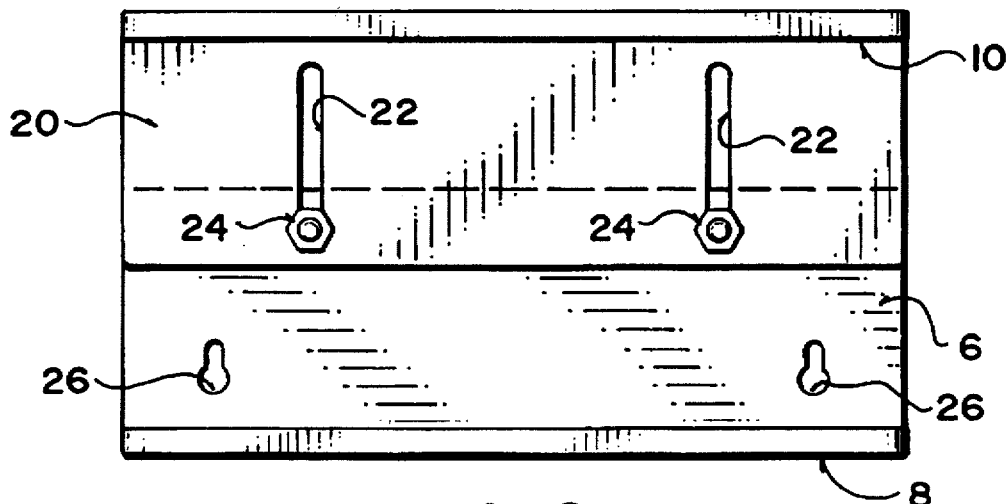
FIG. 9 illustrates a front view of a second embodiment of a restraining device with the upper shelf adjustable for height.

FIG. 9 illustrates a front view of a second embodiment of restraining device 2 with the upper shelf adjustable for height. The second embodiment illustrated in FIG. 9 enables the upper shelf 10 of the restraining device 2 to be raised or lowered in elevation, in order to accommodate different heights of container. The second embodiment is constructed so that the lower shelf 8 is secured to a back plate 6, as with the design illustrated previously in FIGS. 1 through 8 inclusive. However, the upper shelf 10 is secured to a second moveable back plate 20, which is fitted against lower back plate 6. The moveable upper back plate 20 has formed therein a pair of vertical adjustment slots 22. A pair of tightening bolts 24 fit through the respective adjustment slots 22, in corresponding holes drilled in the corresponding locations in the upper regions of the lower back plate 6. The elevation of the upper shelf 10 can be adjusted as required simply by loosening the tightening bolts 24, and allowing the moveable upper back plate 20 to slide upwardly or downwardly as required, to the desired elevation, and then retightening the pair of tightening bolts 24. As seen in FIG. 9, the lower back plate 6 has formed therein a pair of keyhole shaped openings 26, which enable the lower back plate 6, and the entire container restrainer 2, to be mounted on holding screws, or other wall mountings, fixed in a wall at the appropriate spaces. Alternatively, the device can be inverted so that the openings are at the top and the base at the bottom.

Figure 10:
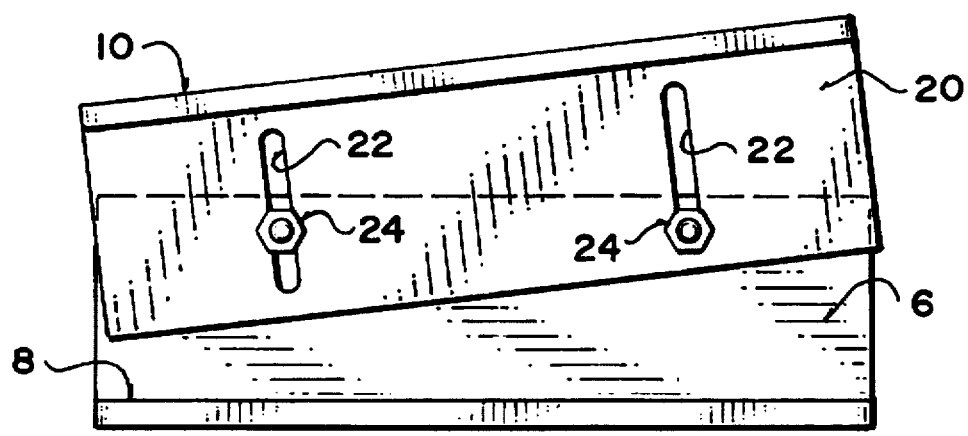
FIG. 10 illustrates a front view of the second embodiment of the restraining device with the upper shelf slanted to accommodate containers of different heights.

FIG. 10 illustrates a front view of the second embodiment of the restraining device, and illustrates how the moveable upper back plate 20 and the upper shelf 10 can be slanted to one side or the other, and the pair of tightening nuts 24 secured in place, thereby enabling the restraining device 2 to accommodate containers of different heights (although the containers are not shown).

Figure 11:
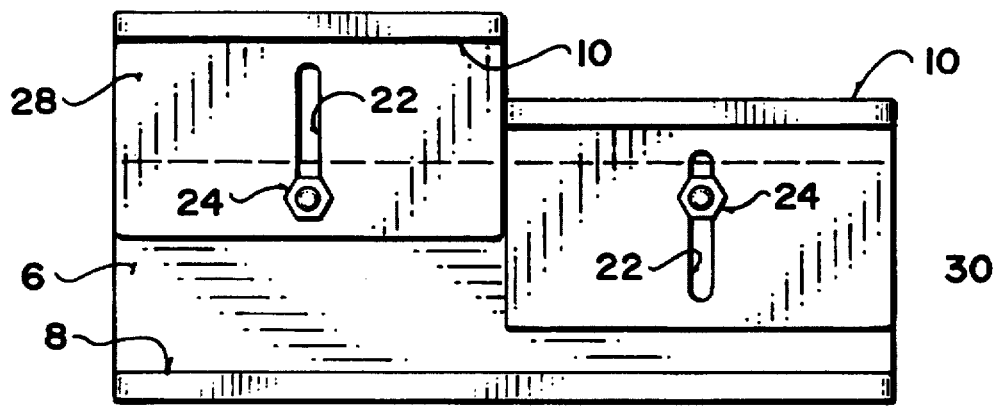
FIG. 11 illustrates a front view of a third embodiment of restraining device with two separately moveable upper shelves, each for holding containers of two different heights.

FIG. 11 illustrates a front view of a third embodiment of restraining device 2, which includes separate left and right adjustable elevation upper shelves. As seen in FIG. 11, the lower portion of the restraining device of the third embodiment is similar to that illustrated previously in FIGS. 9 and 10, namely, the lower part comprises a lower back 6, with a horizontal lower shelf 8. However, the third embodiment includes a left adjustment upper back 28 and a separate right adjustment upper back 30. The left adjustment back 28 has formed therein a vertical adjustment slot 22, while the right adjustment upper back 30 has formed therein a second vertical adjustment slot 22. The left adjustment upper back 28 and right adjustment upper back 30 are each separately held by separate tightening bolts 24. With the third embodiment illustrated in FIG. 11, it is possible to adjust the elevation of the left adjustment upper back 28 so that the upper shelf 10 thereof is at a specified elevation, to accommodate containers of a certain height, while the right adjustment upper back 30 and its upper shelf 10 can be adjusted to a lower elevation to accommodate containers of lesser height.

FIGS. 12 to 33 illustrate how modifications to the basic concept of the invention can be made to accommodate containers of different sizes and shapes within the same restraining frame. Further modifications can be made by the use of gaskets (collars) of various sizes, shape and internal configuration. The restraining collar of the device itself can be crenated in order to accommodate a similarly fashioned collar on the container and, in this way, provide not only fixation within the device but also an inability of the container to rotate within the device.

The restraining device may be mounted to a supporting structure or frame in a variety of ways as illustrated in the orientations in FIGS. 1 to 13. Alternatively, the device may be mounted to a structure by a Velcro™ material which then permits easy release of the restraining device and provides ready mobility within the area required, for example, a clinic or ambulance.

Figure 12:
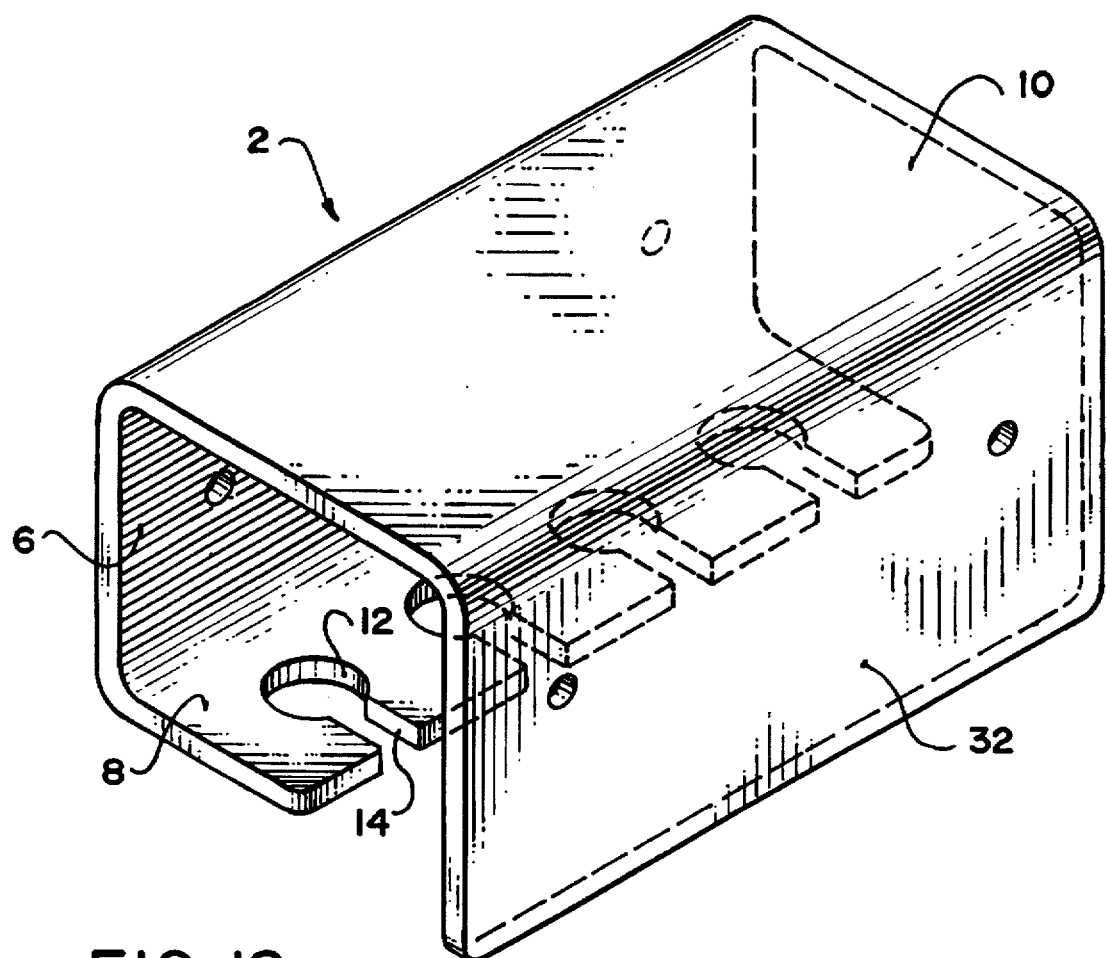
FIG. 12 illustrates an isometric view of a further embodiment of the restraining device which includes a protective shield.
Figure 13:
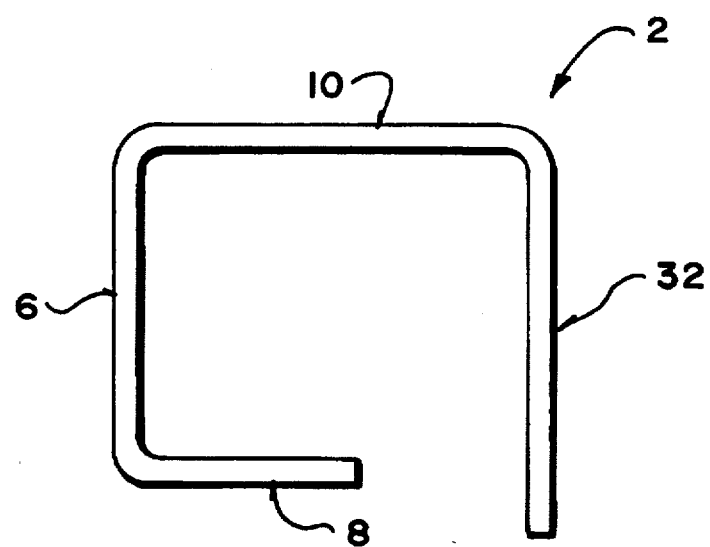
FIG. 13 illustrates a side view of the embodiment of the restraining device with the protective shield.

FIG. 12 illustrates an isometric view of an embodiment of the restraining device which includes a protective shield. FIG. 13 illustrates a side view of the embodiment of the restraining device with the protective shield.

These Figures show a shield 32 in front of the restraining device which can be at a 90 degree angle to the top or at any angle suitable for accessability or for protection from potentially harmful substances. This restraining device can be mounted in any number of ways, for example, as shown in FIGS. 12 and 13, or by the front shield 32 with the back 10 facing the user.

Figure 14:
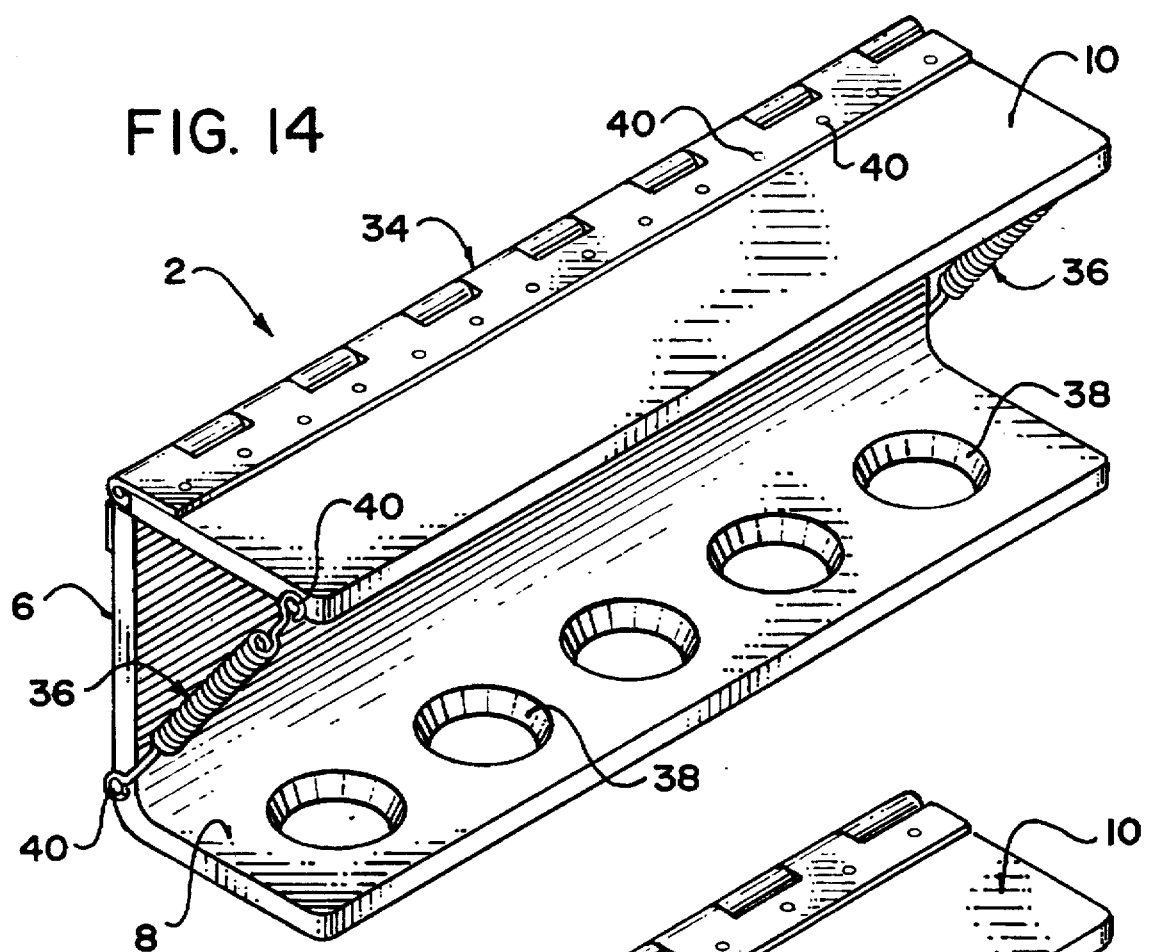
FIG. 14 illustrates an isometric view of a further embodiment of the restraining device including a hinge connecting the upper shelf to the back and a pair of tension coil springs.

FIG. 14 illustrates an isometric view of an embodiment of the restraining device including a hinge for the upper shelf and a pair of tension coil springs. This drawing shows the use of a hinge 34 joining the back 6 to the top 10. The addition of the springs 36 provides the compression force necessary to restrain the containers (not shown). The bottom shelf 8 will now be sufficiently rigid to support larger containers by the use of a holder (not shown) rather than a key slot as shown in previous drawings. This device could be used to restrain large and/or heavy containers. The hinge 34 is secured by screws 40.

Figure 14A:
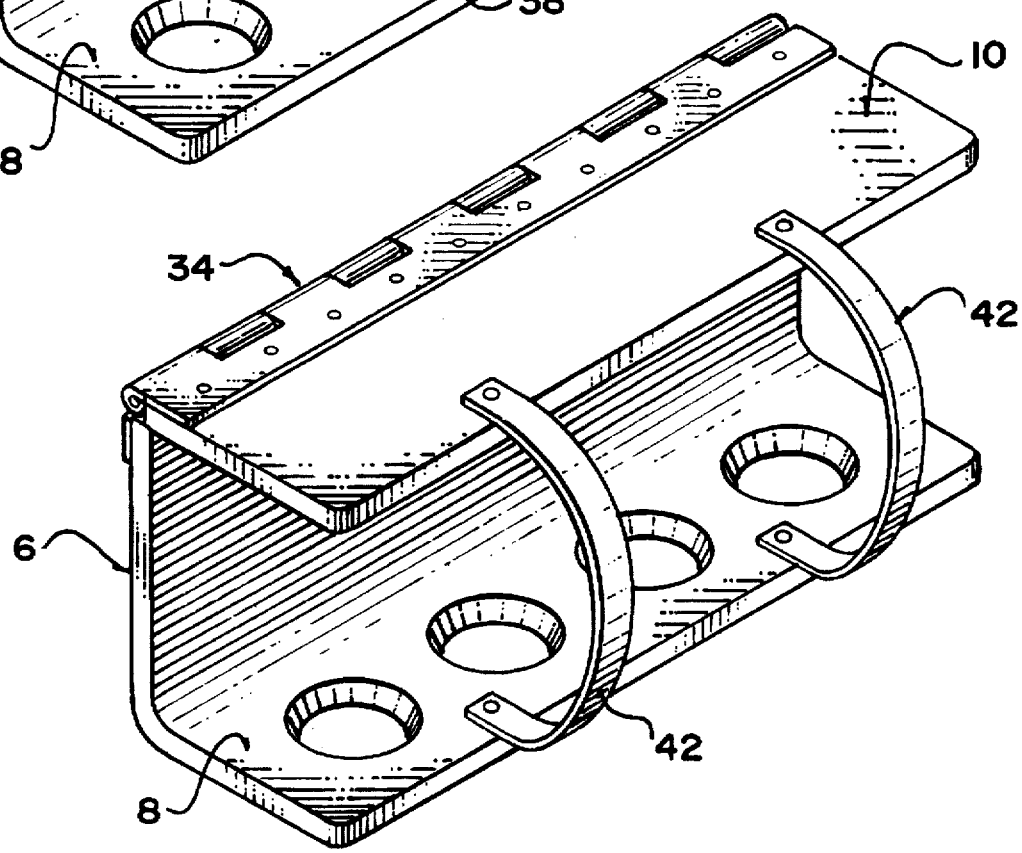
FIG. 14a illustrates an isometric view of a further embodiment of the restraining device with a hinged upper shelf and a pair of clip springs connecting the upper shelf with the lower shelf.

FIG. 14a illustrates an isometric view of an embodiment of the restraining device with a hinged upper shelf and a pair of clip springs 42 connecting the upper shelf with the lower shelf. These can be used in place of the springs 36 illustrated in FIG. 14.

Figure 14B:
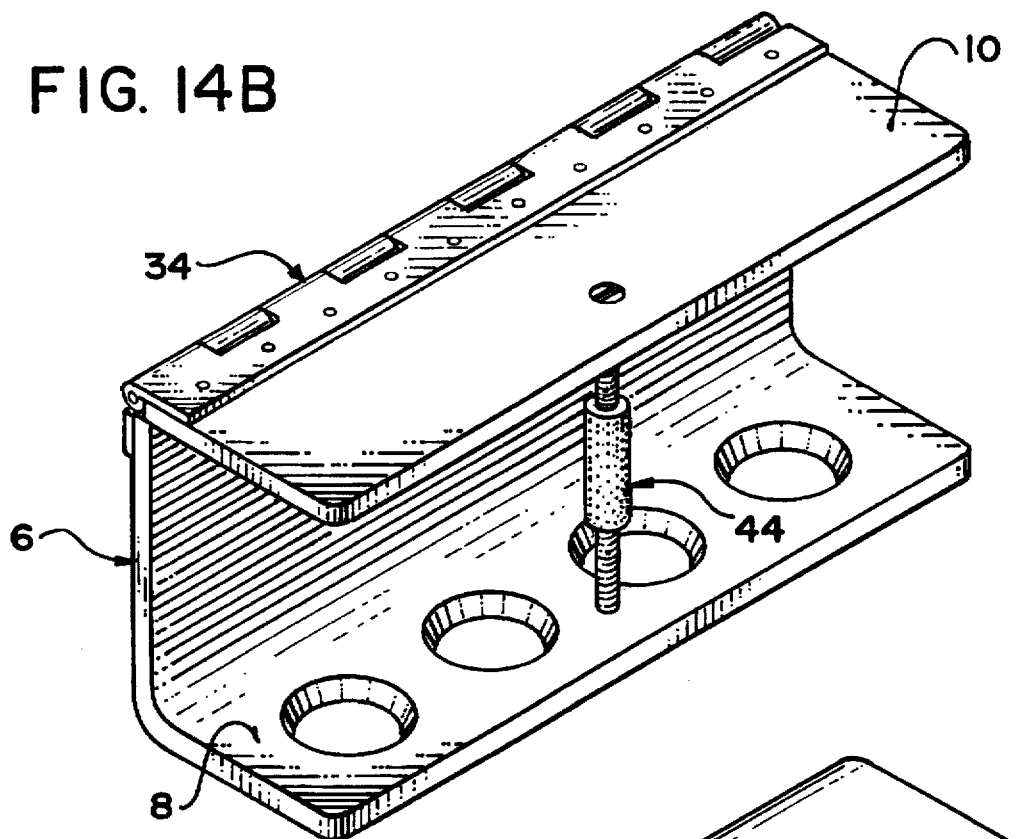
FIG. 14b illustrate an isometric view of a further embodiment of the restraining device with a hinged upper shelf and an adjustable length double screw connecting the upper shelf to the lower shelf.

FIG. 14b illustrates an isometric view of an embodiment of the restraining device with the hinged upper shelf 10 and an adjustable double screw 44 connecting the upper shelf to the lower shelf. The double screw can be adjusted in length and replaces the springs 36 or clips illustrated in FIGS. 14 and 14a respectively.

Figure 15:
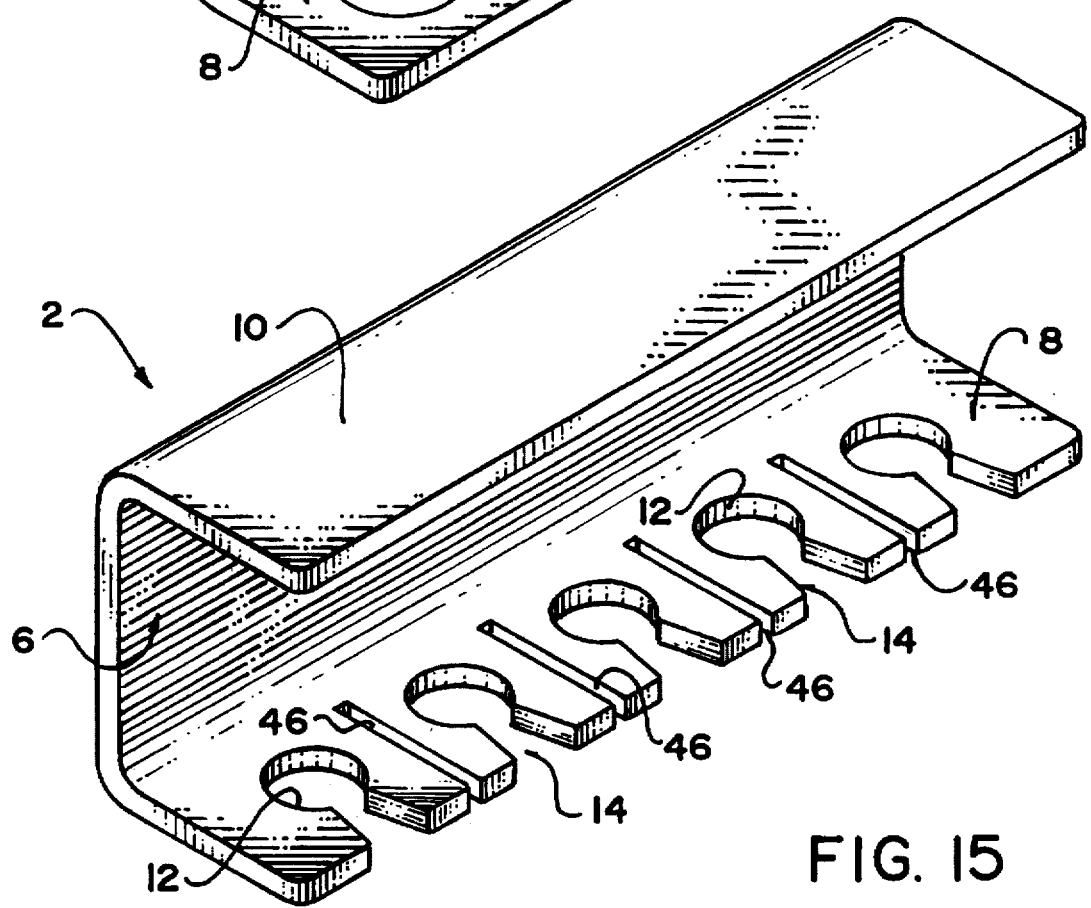
FIG. 15 illustrates an isometric view of a further embodiment of the restraining device with slots between the openings in the lower shelf to provide increased flexibility.

FIG. 15 illustrates an isometric view of the restraining device 2 with a series of parallel slots 46 cut in the lower shelf 8 between the openings 12 to provide increased flexibility for accepting containers.

FIG. 16 illustrates an isometric view of a small size restraining device 48 with a small collar 50 below the opening in the lower shelf of the small restraining device. This is a device for restraining smaller containers. It can be used singularly or inserted in the larger rack 2 to enable containers of varying sizes to be contained in the same restraining device. The device has a collar 50 attached to the bottom to enable it to lock into the corresponding opening 12 in the larger restraining device 2 illustrated in FIG. 1 or FIG. 12. The front face 48 can be used for labelling purposes. The restraining device can secure more than one container by extending its length to include as many as required.

FIG. 17 illustrates an isometric view of a box spacer 52 for connecting the base of a small undersize container between the upper shelf 10 and lower shelf 8 of a standard restraining device 2. FIG. 18 illustrates an isometric view of a container neck collar 54. The collar 54 and spacer 52 are used in combination and allow for various sizes of Containers or objects to be secured within the same restraining device 2. The sizes of the spacers 52 can be varied to fit different size containers as required.

Figure 19:
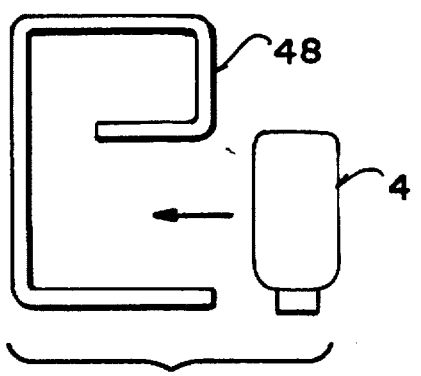
FIGS. 19, 20 and 21 illustrate in sequential side views the method whereby a small container is fitted into a small restraining device, as illustrated previously in FIG. 16.
Figure 20:
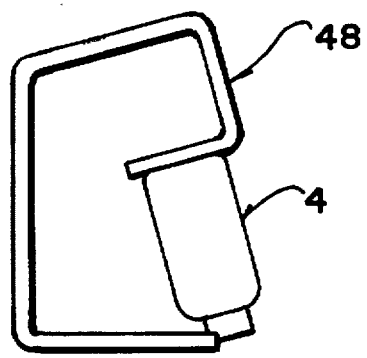
Figure 21:
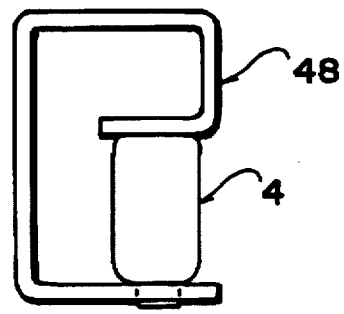

FIGS. 19, 20 and 21 illustrate in sequential side views the method whereby a small container 4 with neck 16 is fitted into a small restraining device 48.

Figure 22:
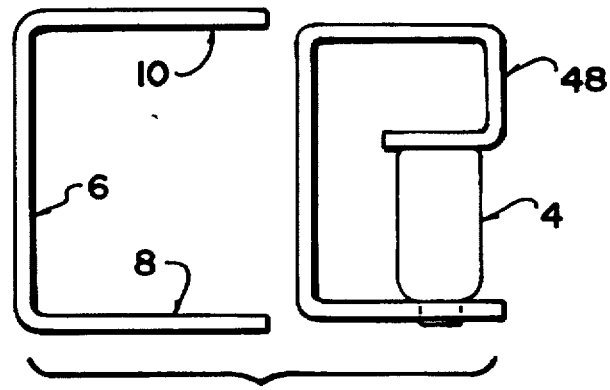
FIGS. 22, 23 and 24 illustrate in sequential side views the method in which a small container releasably held in a small restraining device is fitted into a standard or larger size restraining device.
Figure 23:
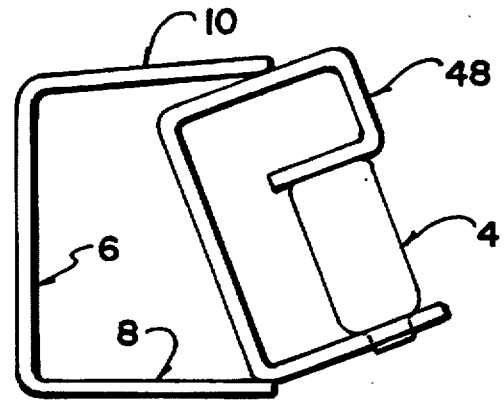
Figure 24:
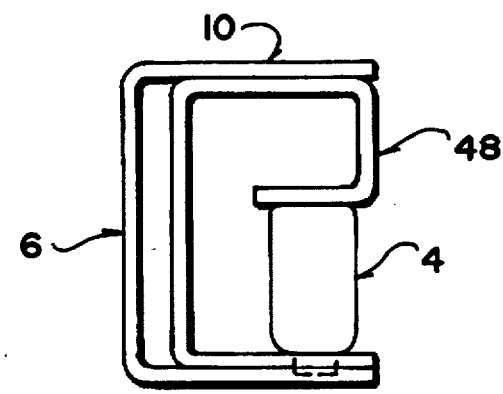
Figure 25:
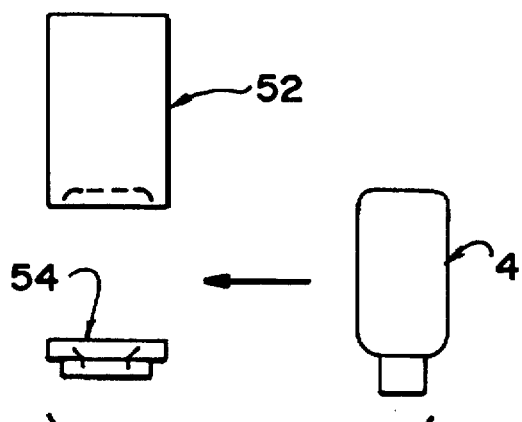
FIGS. 25, 26, 27, 28 and 29 illustrate in sequential side views the method in which a small container is releasably connected with a box spacer and a neck collar and the combination then fitted into a standard size restraining device.
Figure 28:
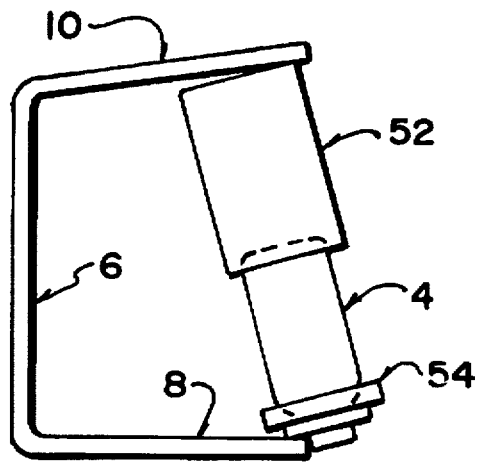
Figure 26:
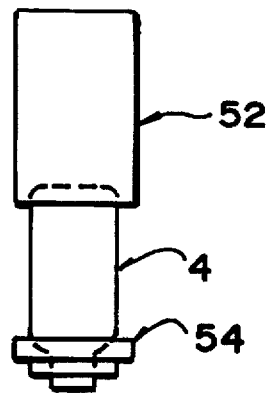
Figure 29:
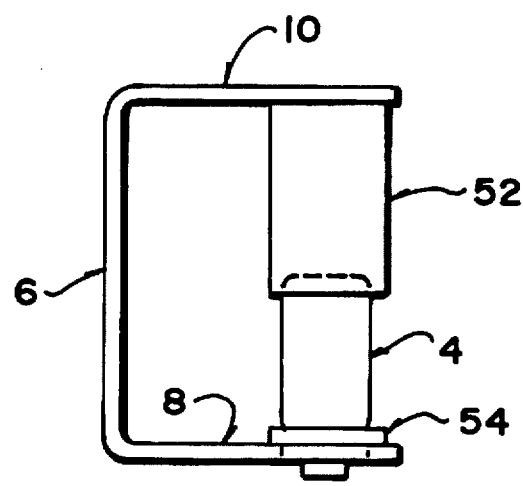
Figure 27:
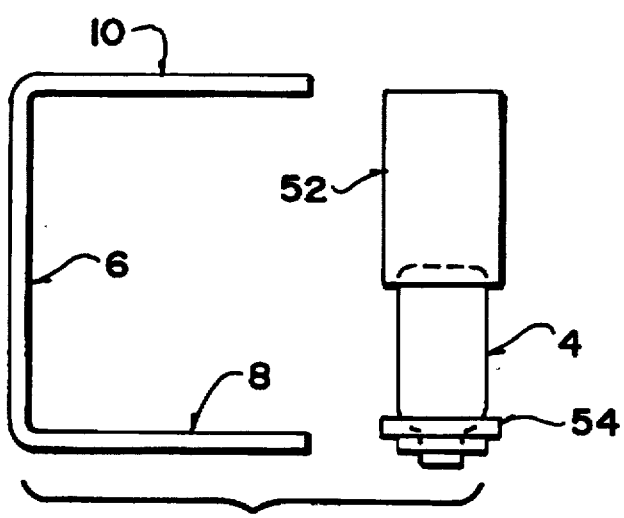

FIGS. 22, 23 and 24 illustrate in sequential side views the method whereby a small container 4 held in a small restraining device 48 is fitted between the upper shelf 10 and lower shelf 8 of a standard size or larger size restraining device 2.

FIGS. 25, 26, 27, 28 and 29 illustrate in sequential side views the method whereby a small container 4 is connected with a box spacer 52 and a neck collar 54 and then fitted between the upper shelf 10 and lower shelf 8 of a standard size restraining device.

Figure 30:
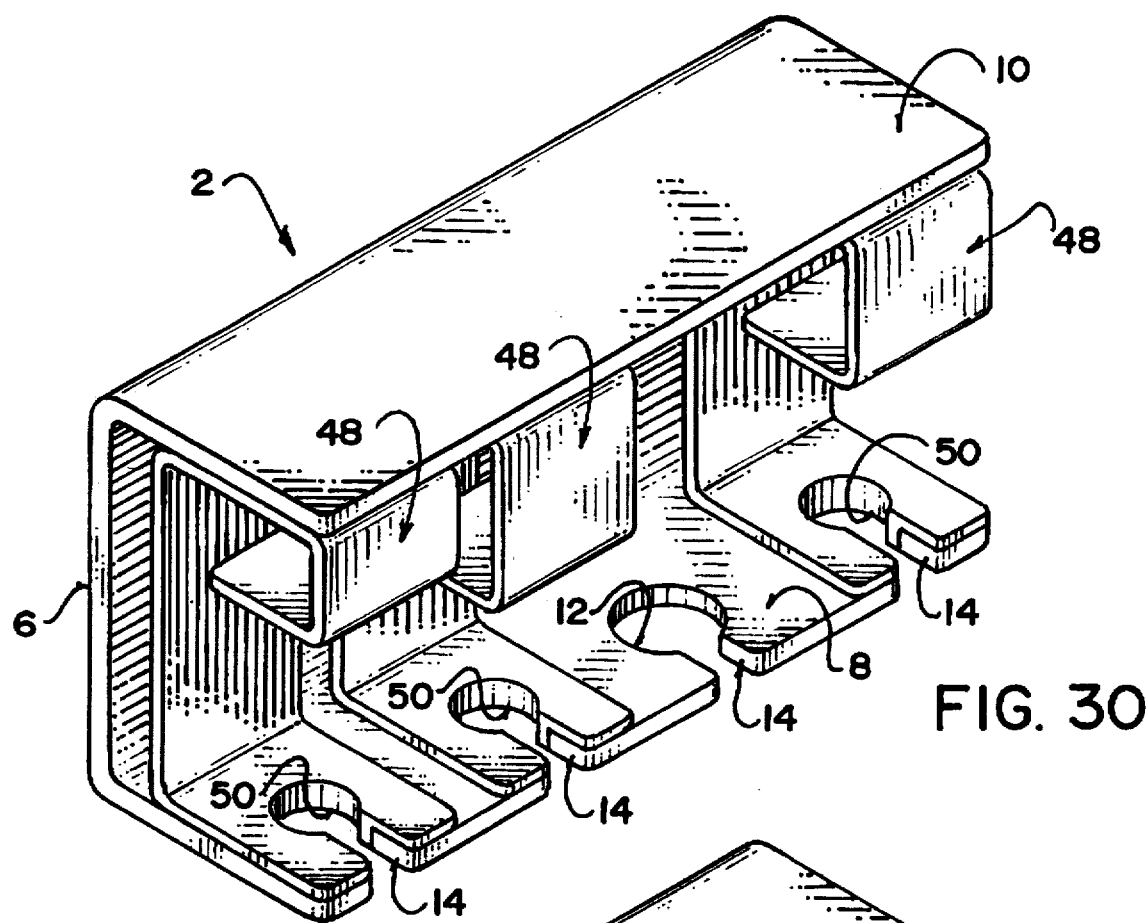
FIG. 30 illustrates an isometric view of a standard size restraining device containing a series of different sizes of small restraining devices, each adapted to accommodate a different size of container.

FIG. 30 illustrates an isometric view of a standard size restraining device 2 containing a series of different sizes of small restraining devices 48, each being of a different size and adapted to accommodate a different size of container (not shown). FIG. 30 shows for illustration purposes how various sized retainers 48 illustrated in FIG. 16 can be inserted in retainer 2 illustrated in FIG. 1 and FIGS. 12, 14 and 15. FIG. 30 specifically shows three different sized small retainers 48 installed in a four slot restrainer 2.

Figure 31:
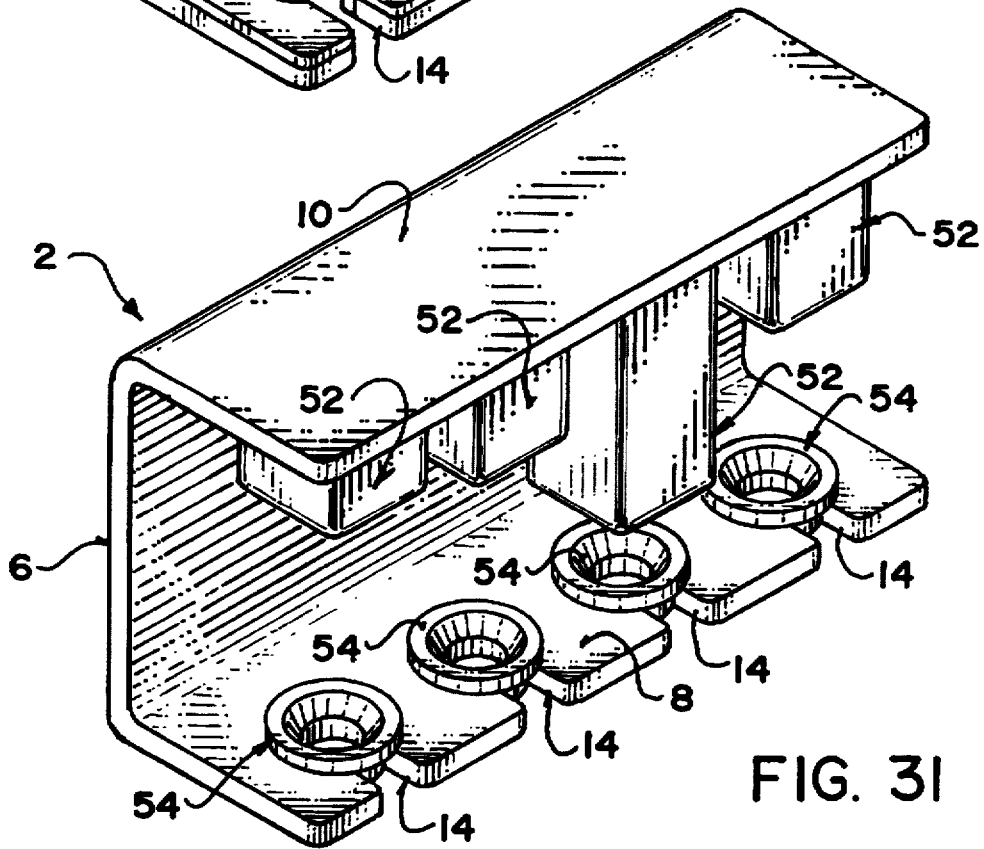
FIG. 31 illustrates an isometric view of a standard size restraining device fitted with a series of box spacers of different sizes, and neck collars, the different sizes of box spacers being adapted to accommodate different sizes of container in one restraining device.

FIG. 31 illustrates an isometric view of a standard size restraining device fitted with a series of box spacers 52 of different sizes, and neck collars 54, the different sizes of box spacers 52 being adapted to accommodate different sizes of container (not shown) in one standard restraining device 2.

Figure 32A:
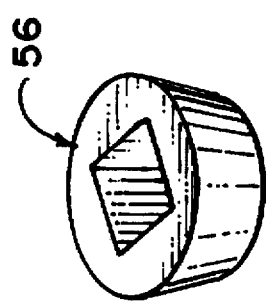
FIG. 32a illustrates an isometric view of a gasket with a square opening.
Figure 32B:
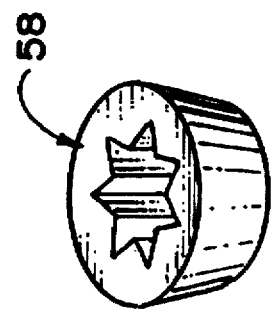
FIG. 32b illustrates an isometric view of a gasket with a crenated opening.
Figure 32:
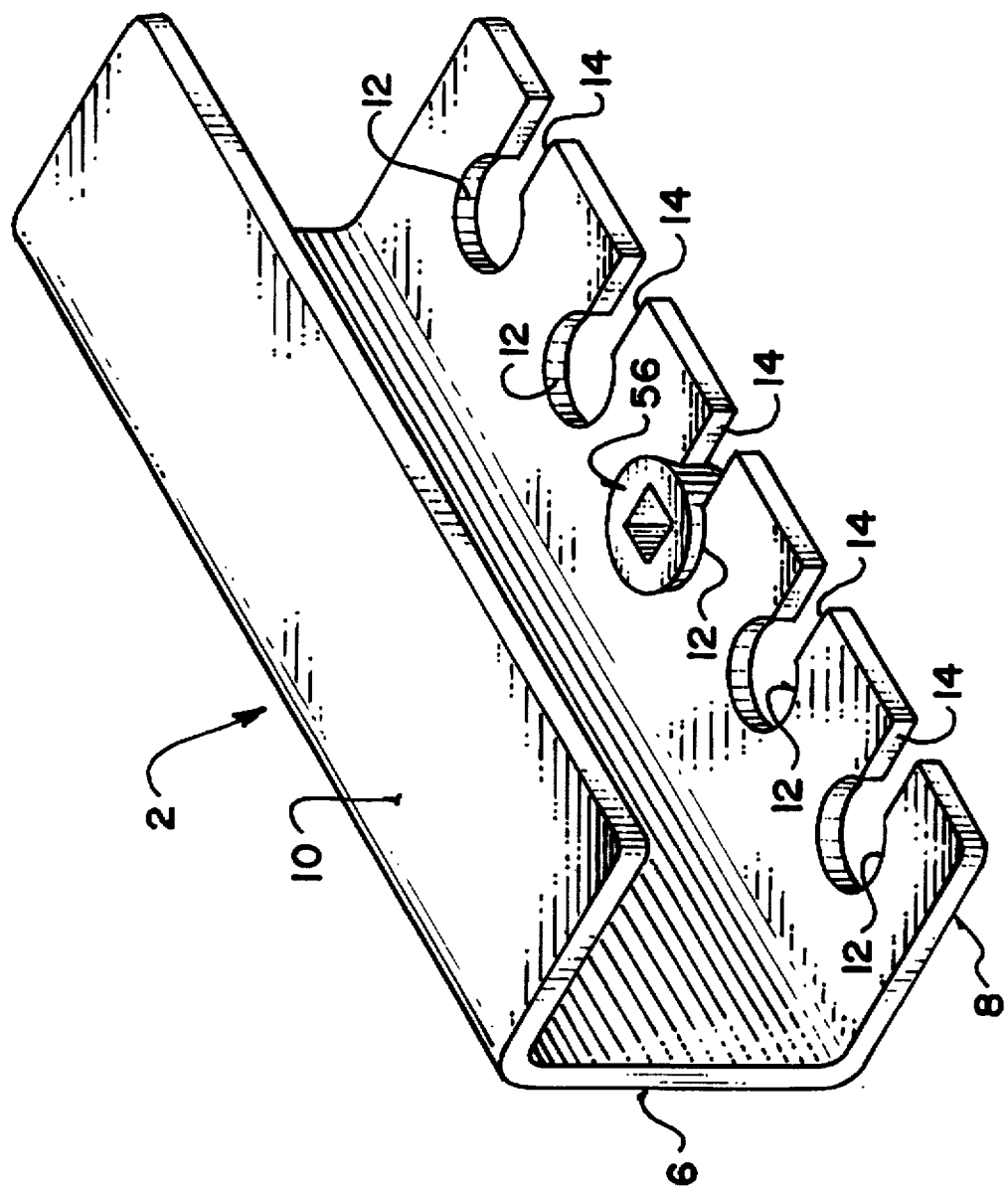
FIG. 32 illustrates an isometric view of a standard size restraining device with a gasket fitted into the central opening of the restraining device.
Figure 33:
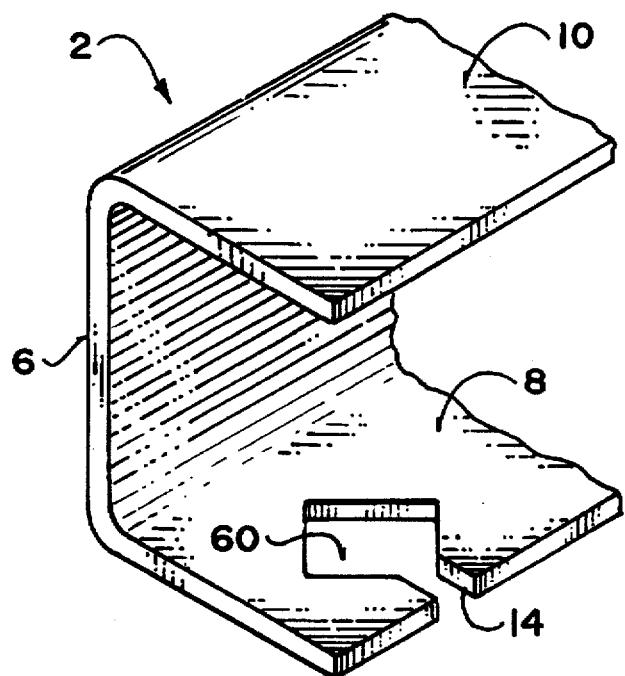
FIG. 33 illustrates an isometric view of a further embodiment of restraining device equipped with a diamond opening instead of a round opening in the lower shelf of the restraining device.
Figure 34:
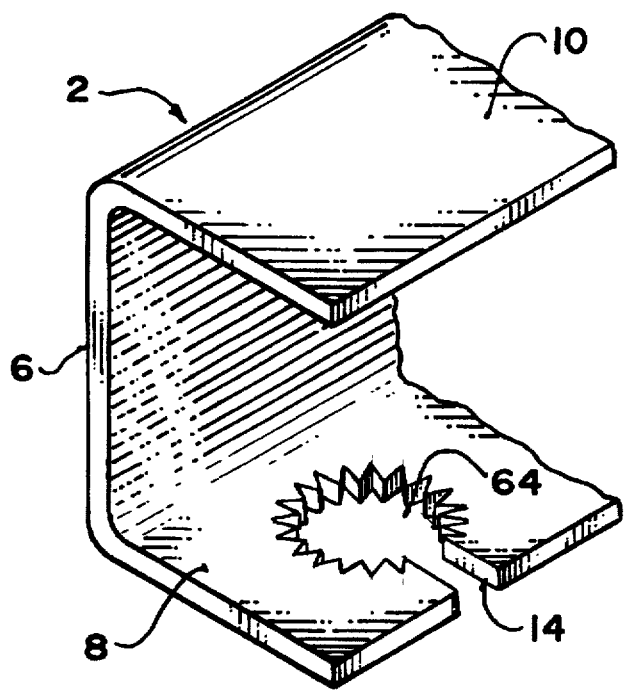
FIG. 34 illustrates an isometric view of a further embodiment of restraining device equipped with a crenated opening instead of a smooth round opening in the lower shelf of the restraining device.

FIG. 32 illustrates an isometric view of a standard size restraining device 2 with a gasket 56 fitted into the central opening 12 of the restraining device 2. This Figure (along with FIGS. 32a and 32b) illustrates examples of various shaped gaskets 56, 58 which are possible to accommodate different container shapes. FIGS. 33 and 34 illustrate isometric views of restraining devices with different shapes of openings and gaskets to accommodate different container shapes. Shapes would conform to the shape of the object/container being secured or a portion of the object/container to be secured. An additional advantage of these designs is that they are capable of locking the object/container in a set position, for example, at the front.

Referring specifically to FIGS. 32 through FIG. 32a illustrates an isometric view of a gasket 56 with a square or diamond shaped opening therein. This fitting will secure a square or diamond shaped object.

FIG. 32b illustrates an isometric view of a gasket 58 with a crenated opening therein. The projections of the crenated opening exert a secure restraining grip on the object or container to be secured.

Figure 33A:
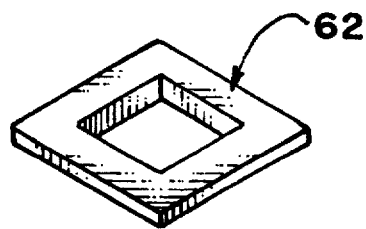
FIG. 33a illustrates an isometric view of a square-shaped fitting with a square opening, adapted to fit into the square opening of the embodiment of restraining device illustrated in FIG. 33.

FIG. 33 illustrates an isometric view of a further embodiment of restraining device 2 equipped with a square or diamond shaped opening 60 instead of a round opening in the lower shelf 8. FIG. 33a illustrates an isometric view of a square shaped collar 62 with a square opening therein, adapted to fit into the square opening 60 of the embodiment of restraining device illustrated in FIG. 33.

FIG. 34 illustrates an isometric view of a further embodiment of restraining device 2 equipped with a crenated shaped opening 64 instead of a smooth round opening in the lower shelf 8 of the restraining device 2. The crenated opening 64 can provide a firm grip to the neck of the container or can accommodate a complementary shaped collar 34a.

Figure 34A:
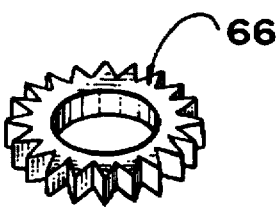
FIG. 34a illustrates an isometric view of a gasket with a crenated margin adapted to fit the complementary configuration of the restraining device illustrated in FIG. 34.
Figure 34B:
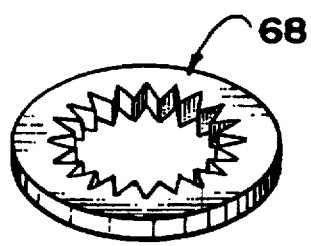
FIG. 34b illustrates an isometric view of a gasket with a crenated aperture, adapted to fit into a round opening in a standard restraining device, such that the gasket provides a secure grip on the neck of a container releasably held in the restraining device.

FIG. 34a illustrates an isometric view of a gasket 66 which can be constructed of rubber, with a crenated margin adapted to fit in the complementary crenated opening 64 of the embodiment of restraining device illustrated in FIG. 34. FIG. 34b illustrates an isometric view of a gasket 68 with a crenated opening, which is adapted to fit into a round opening in a standard restraining device 2. It provides a secure restraining grip on the neck of a container or object releasably held in the restraining device 2.

The restraining device according to the invention fulfils the following criterion and is constructed according to the following specifications:

1. Fixation of the container or object is achieved within the restraining device specifically as a result of securing the neck of the container or object in a custom designed opening in one limb of the frame and applying by means of the other lines a compression force to the base of the container or object due to the inherent elasticity in the frame as a result of its design and manufacture, or as provided by springs or some other mechanism. The shape of the opening may be of any shape or design and can be custom made to specifically secure and fixate the neck of the container or object.
2. The restraining device can be mounted or Used in an upright, erect, horizontal, vertical or inverted manner, as required.
3. The restraining device may be of any size and can be made to accommodate the appropriate dimensions of the specific container or object to be secured.
4. The restraining device may be made of any material, including synthetic plastics, metal or preformed wood. In addition, the restraining device can be made in the form of a wire frame type structure constructed of metal or plastic.
5. The restraining device can be constructed to hold a single container or object or multiple containers or objects. In addition, the restraining device can be constructed so that different size containers or objects within the restraining device can be accommodated individually by division of the frame along the base, or the use of different fittings.
6. The restraining device can be designed to secure containers of various sizes within the same frame by the addition of a platform to the base or to the neck of the restraining device. Containers of different size can also be secured within the same frame by customizing the opening at the top or bottom of the restraining device to accommodate the neck of the appropriate container.
7. The base of the frame of the restraining device may be smooth, recessed or open to accommodate a variety of conformations of the appropriate container.
8. The front side of the restraining device can be used for mounting, carrying or viewing the various containers.
9. Access to the container may be achieved from the top, bottom or sides of the restraining device.
10. The restraining device may be used as an access restricting mechanism for containers where it is desirable to minimize breakage or spillage of the containers, or the containers contain potential harmful or dangerous substances.
11. Additional force to the base of the container can be applied by adding springs or clamps to the open side of the restraining device.

12. The top or bottom shelf of the restraining device can be hinged to provide ready access and can then be secured by clamping or springs.

13. The restraining device can be modified with different gaskets, collars, spacers, and fittings to accommodate different sizes and shapes of containers or objects within the same frame.

14. The restraining device can lend itself readily to the securement of bottle shaped containers, or other objects of virtually any shape including spherical objects such as golf balls and pool balls, by modifying the basic design using appropriate fittings.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A restraining device for an object having opposing first and second ends, said restraining device having a C-shaped profile comprising:
   (a) a back member;
   (b) a first limb associated with the back wherein said first limb acts as a first restraining member for releasably securing and applying a restraining force to the first end of the object;
   (c) a second limb associated with the back member, separate from the first limb, whereby the second limb is adjustable in position relative to the first limb to provide varying distances between the second limb and the first limb, and the second limb acts as a second restraining member for applying a restraining force on the second end of the object, to thereby releasably secure the object between the first and second restraining members; and
   (d) an opening in the first limb adapted to receive a corresponding shape on the object.

2. A restraining device as claimed in claim 1 wherein the first and second restraining members are adjustable in position relative to one another by means of a slot formed in one of the restraining members, and a restraining securing mechanism extending through the slot and securing the first restraining member to the second restraining member.

3. A restraining device as claimed in claim 1 wherein the opening has a removable collar which has a shape that complements an end of the object.

4. A restraining device as claimed in claim 1 wherein the second limb comprises two separate elements, namely a first second-limb-element and a second-limb-element, wherein the first and second-limb-elements are individually adjustable in position relative to one another and to the first limb to provide varying distances between the first and second-limb-elements and the first limb of the restraining device.

5. A restraining device as claimed in claim 1 including a protective shield extending from a free edge of the second limb of the restraining device and extending towards the first limb to protect at least a portion of an open side of the C-shaped restraining device.

6. A restraining device as claimed in claim 5 wherein the shield is a rigid member and attached to the second limb such that the shield is usable as a mounting plate.

7. A restraining device as claimed in claim 1 wherein the first limb has formed therein at least two openings spaced from one another, and a slot is present between each opening but not connecting with the openings.

8. A restraining device as claimed in claim 1 including a spacer which fits between said second limb and the second end of the object and a collar fitted around a circumference of said opening in said first limb.

9. A restraining device as claimed in claim 1 for holding a plurality of objects which are containers having necks, wherein the restraining device has a plurality of openings in the first limb and the device includes a plurality of gaskets fitting into the plurality of openings of the restraining device, and said plurality of gaskets each including an opening therethrough for fitting about the respective necks of the containers.

10. A restraining device for restraining an object having opposing first and second ends, said device comprising:
    (a) a back member;
    (b) a first limb associated with the back member wherein said first limb acts as a first restraining member of the device for releasably securing and applying a restraining force to the first end of the object;
    (c) a second limb associated with the back member, wherein said second limb, said first limb and said back member are arranged in a C-shaped configuration, said second limb acts as a second restraining member for releasably restraining the second end of the object and applying a restraining force on the second end of the object, to thereby releasably secure the object in the restraining device; and
    (d) a hinged mechanism attached to the second limb and to the back member; and
    (e) a spring means which exerts a compression force drawing the second limb towards the first limb.

11. A restraining device as claimed in claim 10 wherein the spring means is a coil spring.

12. A restraining device as claimed in claim 10 wherein the spring means is a spring steel clip.

13. A restraining device as claimed in claim 10 the spring means is a co-axial pair of adjustable screws.

14. A restraining device as claimed in claim 10 further comprising an opening in the first limb and a removable collar releasably attached to an edge of the opening.

15. A restraining device having a C-shaped configuration for restraining an object having opposing first and second ends, said device comprising:
    (a) a back member;
    (b) a first limb associated with the back member, wherein said first limb acts as a first restraining member of the device for releasably securing and applying a restraining force to the first end of the object;
    (c) a second limb associated with the back member wherein said second limb acts as a second restraining member for releasably restraining a second end of the object and applying a restraining force on the second end of the object, to thereby releasably secure the object in the restraining device;
    (d) an opening in the first limb which corresponds in shape to one of the ends of the object; and
    (e) a second restraining device of smaller size for receiving an object of smaller size and fitting into a space between the first and second limbs of the C-shaped restraining device.

16. A restraining device as claimed in claim 15, including a plurality of restraining devices of smaller size fitted in series into the space between the first and second limbs of the C-shaped restraining device.

17. A restraining device for restraining an object, said object having opposing first and second ends, said device comprising:

(a) a back member;

(b) a first limb associated with the back member, wherein said first limb acts as a first restraining member of the device for releasably securing and applying a restraining force to the first end of the object and said first limb has an opening which corresponds in shape to the first end of the object;

(c) a second limb associated with the back member wherein said back member, said first limb, and said second limb are arranged in a C-shaped configuration, and said second limb acts as a second restraining member for releasably restraining a second end of the object and applying a restraining force on the second end of the object, to thereby releasably secure the object in the restraining device;

(d) a gasket which fits around a circumference of the opening, and for releasably securing the first end of the object to the restraining device; and (e) a protective shield extending from a free edge of the second limb of the restraining device and extending towards the first limb covering at least a portion of an open side of the device opposite a side defined by the back member, wherein the shield is usable as a mounting plate.

18. A restraining device for restraining an object, said object having opposing first and second ends, said device comprising:

(a) a back member;

(b) a first limb associated with the back member, wherein said first limb acts as a first restraining member of the device for releasably securing and applying a restraining force to the first end of the object and the first limb has formed therein at least two openings which correspond in shape to the first end of the object, and said openings are spaced from one another, and a slot is present between said openings but not connecting with the openings;

(c) a second limb associated with the back member wherein said back member, said first limb, and said second limb are arranged in a C-shaped configuration, and said second limb acts as a second restraining member for releasably restraining a second end of the object and applying a restraining force on the second end of the object, to thereby releasably secure the object in the restraining device; and (d) a gasket which fits around circumferences of the openings, and for releasably securing the first end of the object to the restraining device.

\* \* \* \* \*

UNITED STATES PATENT AND TRADEMARK OFFICE
CERTIFICATE OF CORRECTION

PATENT NO. : 5,704,495
DATED : January 6, 1998
INVENTOR(S) : Michael S. Bale, et al.

It is certified that error appears in the above-indentified patent and that said Letters Patent is hereby corrected as shown below:

Column 4, line 5, delete "illustrate" and insert --illustrates--.

Column 9, line 48, after "through", insert --34,--.

Column 11, line 51, claim 4, insert --second-- before "second-limb-element" (second occurrence).

Column 11, line 52, claim 4, insert --second-- before "second-limb-elements".

Column 11, lines 54-55, claim 4, insert --second-- before "second-limb-elements".

Column 12, line 36, claim 13, after "claim 10", insert --wherein--.

Signed and Sealed this

Seventh Day of July, 1998

Attest:

*Attesting Officer*

BRUCE LEHMAN

*Commissioner of Patents and Trademarks*